United States Patent [19]

Warriner

[11] Patent Number: Plant 5,640

[45] Date of Patent: Jan. 21, 1986

[54] ROSE PLANT JACHSE

[75] Inventor: William A. Warriner, Tustin, Calif.

[73] Assignee: Jackson & Perkins Company, Medford, Oreg.

[21] Appl. No.: 596,829

[22] Filed: Apr. 4, 1984

[51] Int. Cl.[4] ..... A01H 5/00

[52] U.S. Cl. ..... Plt./18

[58] Field of Search ..... Plt./18

*Primary Examiner*—Robert E. Bagwill

*Attorney, Agent, or Firm*—Klarquist, Sparkman, Campbell, Leigh & Whinston

[57] ABSTRACT

A hybrid tea rose variety having an upright plant, bud and flower color between yellow and light orange, large, ovoid buds opening to imbricated flowers, brownish-colored new foliage, very little fragrance, and good resistance to rose powdery mildew.

1 Drawing Figure

1

This present invention relates to a new and distinct variety of rose plant of the hybrid tea class which was originated by me by crossing the variety Sunshine with an unnamed variety.

The primary objective of this breeding was to produce a new rose variety combining the upright character of both parents with bloom color containing yellow and orange pigments, large and numerous flowers. This objective was substantially achieved along with other desirable improvements as evidenced by the following unique combination of characteristics which are outstanding in the new variety and which distinguish it from its parents, as well as from all other varieties of which I am aware:

1. An upright hybrid tea type plant.
2. Bud and flower color blending between yellow and very light orange.
3. Large, ovoid buds opening to loosely imbricated open flowers.
4. New foliage of a brownish hue comparable to R.H.S. Greyed Orange 174A and B.
5. Very little fragrance.
6. Good resistance to rose powdery mildew.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Sunshine.

*Pollen parent.*—Unnamed variety.

Classification:

*Botanical.*—Rosa hybrid.

*Commercial.*—Hybrid Tea.

2

FLOWER

Observations made from specimens grown at Irvine, Calif. in November.

Blooming habit: Continuous.

Bud:

*Size.*—1¼" when petals start to unfurl.

*Form.*—Pointed ovoid.

*Color.*—When sepals first divide, Yellow-Orange 22C and lighter near distal end. When half blown; upper side of petals ranging from Yellow-Orange 16B at base to Orange 27C with darker veination; lower side of petals mostly Yellow-Orange 16B.

*Sepals.*—Color: Outer surface Green 138A, surface slightly glandular. Three appendaged sepals lightly appendaged. Two unappendaged sepals hairy edged.

*Receptacle.*—Color: Green 138A. Shape: Funnel. Size: Large. Surface: Smooth.

*Peduncle.*—Length: Short. Surface: Glandular. Color: Light green. Strength: Stiff, erect.

*Opening.*—Spiral.

Bloom:

*Size.*—Large. Average open size: 5"–5½".

*Borne.*—Singly.

*Stems.*—Long, strong.

*Form.*—When first open, high centered. Permanence: Outer petal edges slightly curled.

*Petalage.*—Number of petals under normal conditions: 30–35.

*Color.*—Center of flower: Upper side of petals Yellow-Orange 16B; reverse side of petals Yellow-Orange 16B; base of petals Yellow-Orange 16B. Major color: Orange 27B.

*Variegations.*—Occasional weather-related reddish areas.

*Discoloration.*—General tonality at end of first day: No change. Third day: Generally lighter to Orange 27C or Orange 27D.

*Fragrance.*—Slight.

Petals:

*Texture.*—Thick.

*Shape.*—Round.

*Form.*—Edges slightly quilled.

*Arrangement.*—Loosely imbricated. Petaloids in center: few to none.

*Persistence.*—Drop off cleanly.
*Lastingness.*—On the plant, long. As cut flower, long.

Reproductive parts:
*Anthers.*—Medium, many. Color: Yellow. Arrangement: Regular around styles.
*Filaments.*—Color: Yellow.
*Pollen.*—Lemon yellow.
*Styles.*—Color: Reddish.
*Stigmas.*—Color: White.

PLANT

Form: Bush.
Growth: Vigorous, upright, with plant reaching height of approximately 5 feet at Irvine, Calif.
Foliage: Number of leaflets on normal mid-stem leaves: 5.
*Size.*—Medium.
*Quantity.*—Normal.
*Color.*—New foliage: Near Greyed Orange 174A to 174B. Old foliage: Dark green.
Leaflets:
*Shape.*—Broadly oval.
*Texture.*—Leathery on upper side.
*Edge.*—Serrated.
*Serration.*—Single, small.

*Petiole.*—Rachis: Color: Green. Underside: Few prickles.
*Stipules.*—Long, bearded.
*Disease resistance.*—Normally resistant to mildew, blackspot under normal growing conditions at Irvine, Calif.

Wood:
*New wood.*—Color: Reddish. Bark: Smooth.
*Old wood.*—Color: Green. Bark: Smooth.

Prickles:
*Quantity.*—On main stalks from base: Many. On laterals from stalk: Many.
*Form.*—Long, straight.
*Color when young.*—Brown.
*Position.*—Irregular.

Small prickles:
*Quantity.*—On main stalks: few. On laterals: few.
*Color.*—Brown.

I claim:

1. A new and distinct variety of rose plant of the hybrid tea class, substantially as herein shown and described, characterized particularly as to novelty by the unique combination of its upright plant, mildew resistant foliage, flower color of yellow to light orange, and little or no fragrance.

* * * * *

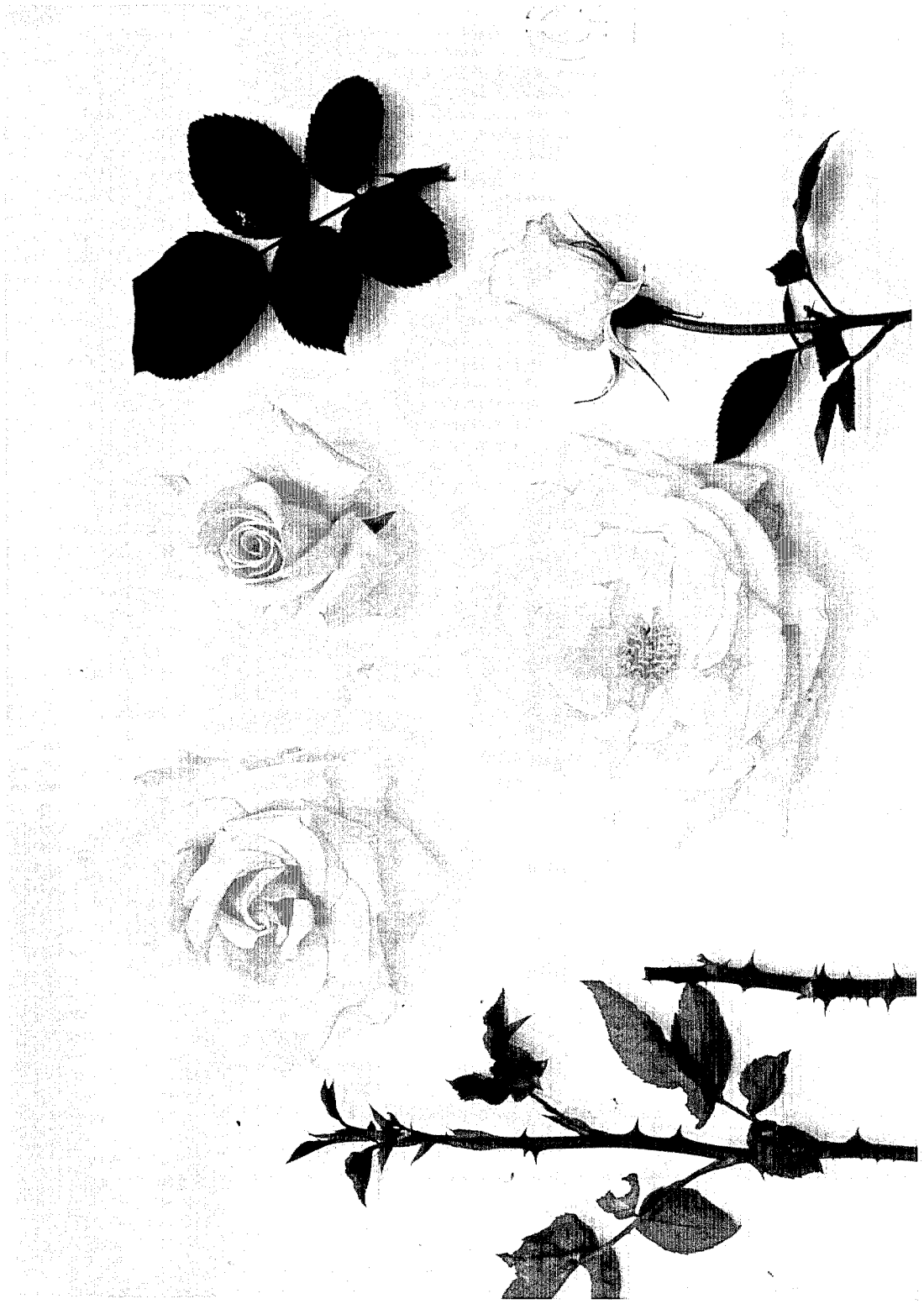

UNITED STATES PATENT AND TRADEMARK OFFICE

CERTIFICATE OF CORRECTION

PATENT NO. : Plant Patent No. PP 5640

DATED : January 21, 1986

INVENTOR(S) : William A. Warriner

It is certified that error appears in the above-identified patent and that said Letters Patent is hereby corrected as shown below:

In the Title:

"JACHSE" should be --JACSHE--.

Signed and Sealed this

*Sixteenth* Day of *September 1986*

[SEAL]

*Attest:*

DONALD J. QUIGG

*Attesting Officer*

*Commissioner of Patents and Trademarks*